United States Patent [19]

Saffell

[11] Patent Number: 5,235,526
[45] Date of Patent: Aug. 10, 1993

[54] MULTI-PROBED SONDE INCLUDING MICROPROCESSOR

[75] Inventor: John R. Saffell, Honiton Devon, England

[73] Assignee: Solomat Limited, Hertfordshire, England

[21] Appl. No.: 619,288

[22] Filed: Nov. 27, 1990

[51] Int. Cl.⁵ ............................................. G01R 31/12
[52] U.S. Cl. ............................... 364/556; 364/571.01; 73/1 R
[58] Field of Search ............... 364/556, 550, 551.01, 364/573, 480, 481, 571.01; 73/1 R; 324/73,1, 115, 132

[56] References Cited

U.S. PATENT DOCUMENTS

| | | | |
|---|---|---|---|
| 4,260,950 | 4/1981 | Hadden et al. | 73/1 R |
| 4,473,797 | 9/1984 | Shiota | 324/115 |
| 4,503,707 | 3/1985 | Rosa et al. | 364/556 |
| 4,600,494 | 7/1986 | Bromberg et al. | 73/1 R |
| 4,608,532 | 8/1986 | Ibar et al. | 364/556 |
| 5,004,998 | 4/1991 | Horii | 364/551.01 |

Primary Examiner—Parshotam S. Lall
Assistant Examiner—Michael Zanelli
Attorney, Agent, or Firm—Seidel, Gonda, Lavorgna & Monaco

[57] ABSTRACT

A sonde is provided which includes a plurality of discrete sensing electrodes of analog output projecting from a housing within which are accommodated a microprocessor and an analog-digital converter to digitize the output of the electrodes. A stirrer is fully integrated into the housing and projects from the housing centrally with the electrodes around it. The stirrer motor and the stirrer control are integrated into the housing. The microprocessor controls the stirrer control. The sonde also has a readily attachable and detachable calibration cup with wells defined therein. Each well is designed to receive its own liquid. The calibration cup is designed such that all the electrodes can be calibrated simultaneously.

31 Claims, 9 Drawing Sheets

MULTI-PROBED SONDE INCLUDING MICROPROCESSOR

FIELD OF THE INVENTION

The present invention relates to an improved sonde for measuring electrical magnitudes or values linked with electrical magnitudes.

Definitions

As used herein, the terms "sonde" and "sonde unit" are used interchangeably to refer to a housing which comprises a plurality of electrodes/probes and circuitry associated therewith.

As used herein, the terms "electrodes", "probes", and "pick-up means" are used interchangeably to refer to a means which monitors specific parameters in a fluid and converts this monitored measurement to an analog signal.

BACKGROUND OF THE INVENTION

In their simplest form, sondes consist of a detecting or sensing element e.g., an electrode, a probe, etc. and electronic circuitry for processing signals supplied by the element. Metering apparatuses also generally comprise a display means or some other means for transmitting the results to users.

Since their introduction into the industry, metering apparatuses have gone through various advancements. An example of one such advancement is the implementation of micro-processors which enable the use of several electrodes or probes within one unit. An example of a multi-probe metering apparatus is disclosed in U.S. Pat. No. 4,608,532, incorporated herein by reference.

Since its introduction into the industry, the multi-probed metering apparatus has been extensively used. In a specific form of conventional multi-probed metering apparatuses, the plurality of electrodes/probes are generally combined into a single mechanical housing referred to hereinafter as a "sonde". This design facilitates transport of the apparatus. Moreover, the implementation of a sonde for the housing of a plurality of electrodes/probes reduces the number of cables and components necessary in such multi-probed devices.

In their simplest form, multi-probed metering apparatuses have the ability to measure a plurality of parameters, one such parameter being associated with each individual electrode/probe. The sonde units of conventional multi-probed devices generally comprise some sort of means for selecting which electrode's/probe's signal will be monitored at a given point in time.

After a particular electrode/probe has been selected, the analog signal produced thereby is processed. This signal can be processed in many different ways. Examples of such ways include: (a) sending the analog signal from the selected electrode/probe directly to an instrument or user for measurement, analysis, calibration, display and/or storage; and/or (b) sending the analog signal from the selected electrode/probe to a central processing unit, wherein the analog signal is first digitalized, and then transmitted to an instrument or user for measurement, analysis, calibration, display and/or storage.

Although they are extensively employed in the industry, many of the conventional multi-probed metering apparatuses have inherent limitations and/or problems associated therewith. These limitations and/or problems are due, in part, to their specific design and/or their limited circuitry.

One major problem associated with many conventional multi-probed metering apparatuses pertains to their inability to consistently reproduce measured parameters accurately, when the signal from the electrode/probe has to be transmitted over a substantial distance. Specifically, sonde units of some multi-probed metering apparatuses first measure a specific parameter and convert this measurement into an analog signal. This signal is then sent to a central processing unit where it is digitalized and/or processed.

When the distance between the sonde unit and the central processing unit is substantial (i.e., generally anything over ten meters), the signal generally begins to deteriorate. This deterioration skews the accuracy of the measurement being monitored.

One method of attempting to overcome this problem is by employing highly-sophisticated analog cabling between the sonde unit and the central processing unit. While this technique can work under certain conditions, it is very expensive. Specifically, high quality analog cabling retails for approximately $3 to $10 per meter. If the sonde unit is employed, for example, to measure various parameters in water at depths of over 100 meters, it can easily be seen how the cost of employing the aforementioned technique to overcome this particular problem can become very expensive.

Another method of attempting to overcome the problem associated with accurately reproducing measured parameters and transmitting these measurements over a substantial distance is by programming the central processing unit to compensate for the deterioration of the transmitted signal. This method can successfully be employed, but only under those circumstances where all other variables (e.g., distance between electrodes and central processing unit, ambient temperature, solution temperature, etc.) remain relatively constant. However, since in the analytical world nothing remains constant, and since multi-probed metering apparatuses are generally used under a multitude of differing conditions, this technique of overcoming the problem is generally unfeasible.

Accordingly, a multi-probed metering apparatus which can accurately reproduce the measurements from its sonde unit, without substantially increasing the cost of the device, would be a welcome improvement in the industry. It would be an even more welcomed improvement if this high level of reproducibility could be accomplished when the sonde unit is a substantial distance from the central processing unit.

Another problem associated with many of the conventional multi-probed metering apparatuses pertains to the scope of their functions (i.e., the flexibility of the metering apparatus). Specifically, many of the conventional multi-probed metering apparatuses have virtually no flexibility since they are merely able to display the monitored information.

Some conventional multi-probed metering apparatuses, however, have associated therewith a limited amount of flexibility due to their capability of being interfaced with other devices. Examples of devices which can be interfaced with some of the conventional multi-probed metering apparatuses include: (a) control means which can trigger various functions such as the sounding of an alarm, the opening/closing of a valve, etc., and/or (b) computers for compiling and/or processing the monitored information.

Due to their limited amount of flexibility, most conventional multi-probed devices are limited, in the field, to their specific internal software design, if any. Therefore, if one desires to change some of the parameters, to analyze a measured parameter, or to calculate a non-measured parameter from measured parameters, traditionally, the metering apparatus has to be interfaced with some sort of external memory storage and/or data processing source (e.g., a computer).

Since it is often desirable to change parameters, analyze measured parameters, and/or calculate non-measured parameters on site, and since it is cumbersome to continually have a computer available, it would be a welcomed improvement in the industry if a multi-probed metering apparatus can be designed to make elaborate mathematical computations without having to be interfaced with an external memory storage and/or data processing source.

When monitoring specific parameters of a fluid with a multi-probed metering apparatus, it is often desirable to have the fluid continually flowing over the electrodes. Therefore, when the fluid is stagnant, an external fluid flow-maintaining means is conventionally employed.

Many of the conventional multi-probed metering apparatuses which employ such a fluid flow-maintaining means do so by the implementation of an external stirrer unit. In conventional apparatuses, this external stirrer unit is an independent component generally attached to the opposing face of the sonde unit such that the propeller of the stirrer unit is pointing back towards the plurality of electrodes/probes. This conventional external stirrer unit is generally connected to the central processing unit by a separate external cable.

While the conventional external stirrer design does maintain the flow of fluid over the electrodes/probes, there are inherent problems associated therewith. One such problem pertains to size. Generally, due to the presence of the external stirrer unit and the separate external cable therefor, the sonde unit becomes bulky and difficult to handle.

Another problem associated with employing an external stirrer component pertains to the separate, external cable between it and the central processing unit. As stated earlier, the sonde unit can be located at distances of over 100 meters from the central processing unit. In the first instance, there is an inherent cost associated with connecting the stirrer to the central processing unit which the user would obviously like to avoid. Furthermore, since the separate cable between the external stirrer unit and the central processing unit is external, it is susceptible to the conditions in which the electrodes have been submerged. These conditions often have an adverse effect on cable, and especially at its connection points. Accordingly, the external cables associated with conventional stirrer units have to be frequently repaired, maintained and/or replaced.

In view of the above, it would also be a welcomed improvement in the industry if a method could be devised to minimize the cost of employing, maintaining and/or replacing the means for maintaining a fluid flow over the electrodes/probes.

Yet another problem associated with the conventional external stirrer units pertains to their amount of energy consumption. Specifically, stirrer units inherently consume a large amount of energy. Since most multi-probed metering apparatuses are commonly used in the field, they are generally run from battery packs. Since the life of a battery depends largely upon the energy being consumed, it is desirable to minimize the amount of energy consumed for extraneous purposes (e.g., running a stirrer). However, as indicated earlier, it is also desirable to have the fluid flowing over the electrodes/probes, as opposed to being stagnant. In view of the above, the industry is faced with a dilemma. Accordingly, it would be another welcomed improvement if a means could be devised to maintain fluid flow over the electrodes/probes, while minimizing the amount of energy consumed.

Yet another problem associated with many of the conventional multi-probed metering apparatuses pertains to their methods of calibration. For example, most multi-probed metering apparatuses are calibrated by the following technique. First, a calibration solution, useful for calibrating one specific parameter (e.g., "zeroing") of one specific electrode/probe, is placed into a calibration bath. Since all electrodes/probes of most conventional metering apparatuses are housed in one sonde unit, all electrodes/probes are dipped into this specific calibration solution. The one electrode/probe relating to the specific calibration solution in the bath is then calibrated.

Thereafter, that particular calibration solution is discarded from the bath; and the electrodes and the solution container are rinsed. This filling-calibration-rinsing process is then repeated for each of the remaining electrodes until all are calibrated for that specific parameter (e.g., zeroed). However, since in many instances electrodes/probes also have to be calibrated for other parameters (e.g., "slopes"), this generally means that the aforementioned filling-calibration-rinsing process has to be repeated for each electrode/probe with a second type of calibration solution.

As can be seen, the conventional method of calibrating multi-probed meters is extremely time-consuming. Moreover, although the electrodes/probes, which have been subjected to the aforementioned conventional calibration technique, are rinsed after each calibration, they are, at least to some degree, contaminated by the other various calibration solutions (e.g., pH electrodes can be contaminated by turbidity calibration solutions). Accordingly, a device or technique which simplifies the calibration of multi-probed metering apparatuses and/or eliminates the contamination of the various electrodes/probes by extraneous, non-related, calibration solutions, will be yet another welcomed improvement in the industry.

Even another problem associated with many of the conventional multi-probed metering apparatuses pertains partially to repairing and/or replacing damaged electrodes/probes, and partially, to changing the parameters which the electrodes/probes monitor. Specifically, since many of the conventional multi-probed metering apparatuses are used to measure various parameters in fluids (e.g., water), the connections between the electrodes/probes and circuitry within the sonde unit must remain dry. Therefore, the sonde unit must be water-tight. Due to this requirement, many sonde units are factory sealed. Therefore, if a particular electrode/probe has to be repaired or replaced for one reason or another, the entire sonde unit generally has to be taken out of commission and returned to a shop where the work can be performed.

If the metering apparatus is being employed to continually monitor specific parameters, this generally requires a user to have more than one sonde unit available on site. Since the sonde units can retail from between $1,000 up to $5,000, depending upon the number of electrodes/probes and the circuitry therein, it is very costly to have a number of sonde units available on site. Accordingly, another welcomed improvement in the industry would be a multi-probed metering apparatus designed for field replacement and/or repair of electrodes/probes without destroying the necessary watertight configuration of the sonde unit.

SUMMARY OF THE INVENTION

It is one object of the present invention to provide an improved multi-probed metering apparatus which can accurately reproduce monitored parameters over substantial distances.

It is another object of the present invention to provide an improved multi-probed metering apparatus which can make multi-pass linearization mathematical computations without having to be interfaced with an external memory storage and/or data processing source.

It is still another object of the present invention to provide an improved means for maintaining fluid flow over the electrodes/probes of a multi-probed metering apparatus.

It is a further object of the present invention to provide a means for minimizing the cost of employing and/or repairing the means for maintaining fluid flow over the electrodes/probes of a multi-probed metering apparatus.

It is still a further object of the present invention to provide a means for minimizing the amount of energy consumption associated with maintaining fluid flow over the electrodes/probes of a multi-probed metering apparatus.

It is even a further object of the present invention to provide an improved multi-probed metering apparatus comprising an improved method of calibration.

It is yet a further object of the present invention to provide a means for field replacing and/or repairing electrodes/probes of a multi-probed metering apparatus.

It is even another object of the present invention to provide an improved metering apparatus which can process the information from a plurality of sonde units.

These and other objects are met by the present invention due to the advent of a novel multi-probed metering apparatus.

One embodiment of the present invention pertains to a novel multi-probed metering apparatus which comprises at least one sonde unit. The at least one sonde unit comprises: (a) a plurality of electrodes/probes and circuitry associated therewith for signal conditioning, (b) an analog/digital converter means, (c) a selector circuit, and (d) a primary digital signal processing circuit. The sonde unit selector circuit identifies each of the plurality of electrodes/probes in order to control the treatment of the signals provided thereby. The selector circuit also interfaces the plurality of electrodes/probes with the analog/digital converter means. The sonde unit primary digital signal processing circuit is in bi-directional digital communication with the analog/digital converter means and in uni-directional digital communication with the selector circuit.

The novel multi-probed metering apparatus of the present invention also comprises a central processing unit. This central processing unit comprises: (a) a power supply for the central processing unit and for the sonde unit, (b) a real-time clock means, (c) a random access memory storage means capable of storing at least 500 bytes of information, (d) an arithmetic and logic unit means capable of making multi-pass linearization mathematical computations, (e) a secondary digital signal processing circuit supplying a digital output, (f) means for processing the digital output from the secondary digital signal processing circuit and (g) a digital output means. The secondary digital signal processing circuit is in bi-directional digital communication with the following components: the sonde unit primary digital signal processing circuit, the real-time clock means, the random access memory storage unit means, the arithmetic and logic unit means and the digital output means.

Another embodiment of the present invention pertains to the multi-probed metering apparatus described above which further comprises an improved fluid flow-maintaining means. The improved fluid flow-maintaining means of the present invention is integrated into the body of the sonde unit, as opposed to being an external fixture thereon. This improved fluid flow-maintaining means comprises: (a) a stirrer control, (b) a stirrer driving component and (c) a propeller means. The stirrer control of this fluid flow-maintaining means is in uni-directional digital communication with both the sonde unit primary digital signal processing circuit and the stirrer motor. The propeller means is typically centrally located between the plurality of electrodes/probes.

Yet a further embodiment of the present invention pertains to the multi-probed metering apparatus described above which further comprises an improved means for calibrating the plurality of electrodes/probes. The improved calibration means of the present invention comprises a calibration cup having defined therein a plurality of vertically-oriented wells passing partially therethrough. The wells are positioned such that they correspond with the configuration of the plurality of electrodes/probes in the sonde unit. Each well is dimensioned to accept the specific electrodes/probe to which it corresponds, while leaving a sufficient gap therearound for fluid flow.

Other objects, aspects and advantages of the present invention will become apparent to those skilled in the art upon reading the following detailed description, when considered in conjunction with the accompanying drawings and appended claims.

BRIEF DESCRIPTION OF THE DRAWINGS

A more complete appreciation of the invention and many attendant advantages thereof will be readily obtained as the same become better understood by reference to the following detailed description, when considered in conjunction with the accompanying figures briefly described below.

DETAILED DESCRIPTION OF THE INVENTION

Figure 1:
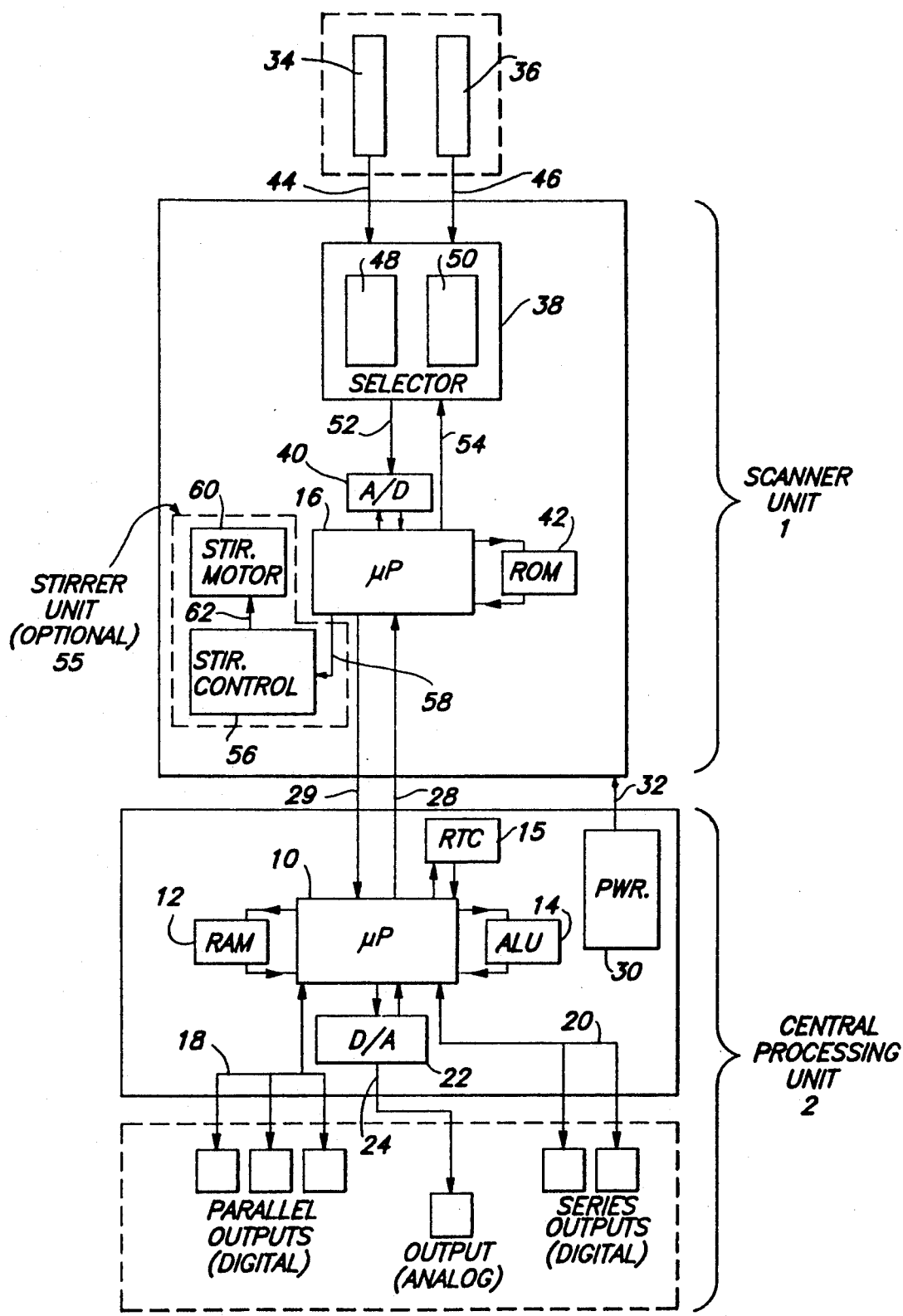
FIG. 1 is an overall schematic circuit diagram of a multi-probed metering apparatus according to one embodiment of the present invention.

The novel multi-probed metering apparatus of the present invention solves many of the problems which have been plaguing the industry for years.

In the most general case of the present invention, analog signals are provided by the electrodes/probes of the sonde unit. These signals are transmitted to an input signal acquisition unit (i.e., an analog/digital converter means) wherein they are digitalized. Generally, the analog/digital converter means is combined with an electronic selector circuit which alternatively selects one or the other of the two routes to which the electrodes/probes are connected.

The now digitalized analog signals are transmitted to a primary digital processing unit in the sonde unit for measurement. The primary signal processing circuit is in bi-directional digital communication with the analog/digital converter means, and is in uni-directional digital communication with the aforementioned electronic selector circuit.

A digital output corresponding to the analog signal from the electrodes/probes is then transmitted from the sonde unit primary digital signal processing circuit to a secondary digital signal processing circuit of the central processing unit. The secondary digital signal processing circuit is in bi-directional digital communication with the following components: the sonde unit primary digital signal processing circuit, a real-time clock means, a random access memory storage means capable of storing at least 500 bytes of information, an arithmetic and logic unit means and a digital output means.

The digitalized signal transmitted from the sonde unit primary digital signal processing circuit is subjected to multi-pass linearization mathematical computations in the central processing unit secondary digital signal processing circuit. During the multi-pass linearization mathematical computations, information is provided to the secondary digital processing circuit by the following components: the random access memory storage unit means, the arithmetic and logic unit means and the real-time clock means.

The secondary digital signal processing circuit, after making the aforementioned computations, produces a digitalized output which can be used as such to determine, for example, whether there is a high level or low level signal, or can be converted to an analog signal by a digital/analog converter means and used as such.

In the sonde unit and the central processing unit of the present invention, there are signal conditioning circuits associated with each specific electrodes/probes.

Multi-pass linearization computations of the signals within the central processing unit simplifies the structure of the sonde unit and reduces costs. Indeed, the measurements to be linearized are supplied by the sonde unit primary digital processing circuit when interfaced with the central processing unit secondary digital processing circuit. Therefore, certain electrodes/probes may have a non-linear response without this complicating the sonde unit to which they are connected.

The junction between the sonde unit and the central processing unit ensures electrical contact between the two elements for the following purposes:

(a) power supply and earthing supplied by the central processing unit to the sonde unit; and (b) bi-directional digital communication between the sonde unit primary digital processing circuit and the central processing unit secondary digital processing circuit.

By converting the analog signals from the electrodes/probes to digital signals in the sonde unit, there need only be bi-directional digital communication between the sonde unit primary digital processing circuit and the central processing unit secondary digital processing circuit. This type of circuitry reduces a number of contacts between the central processing unit and the sonde unit. Moreover, this type of circuitry also eliminates the need of highly-sophisticated analog cabling between the sonde unit and the central processing unit. Therefore, by the implementation of the circuitry in accordance with the present invention, the total number of interface lines between the sonde unit and the central processing unit is substantially reduced. Moreover, the use of analog cabling between the two units is eliminated.

The multi-probed metering apparatus of the present invention will be better understood when described in greater detail with reference to the appended drawings. It should be noted, however, that the following descriptions merely describe embodiments of the present invention and should, in no way, be considered limiting the scope of the present invention.

FIG. 1 illustrates an overall schematic circuit diagram of a multi-probed metering apparatus according to one embodiment of the present invention. The apparatus illustrated in FIG. 1 comprises one sonde unit generally referred to as item 1 and one central processing unit generally referred to as item 2. As will be shown later (i.e., in FIGS. 2 and 3), the multi-probed metering apparatuses of the present invention can comprise a plurality of sonde units.

The central processing unit 2 comprises secondary digital signal processing circuit (i.e., micro-processor 10). The micro-processor is in bi-directional digital communication with the following components: (a) random access memory storage unit means (i.e., RAM 12), (b) arithmetic and logic unit means (i.e., ALU 14) capable of making multi-pass linearization mathematical computations, (c) real-time clock means (i.e., RTC 15), (d) and the sonde unit primary digital processing circuit (i.e., micro-processor 16) and (e) the digital output means.

Micro-processor 10 produces a digital output which is transmitted to a digital output means. The communication between the central processing circuit secondary digital signal processing circuit and the digital output means can be in direct contact, in parallel form via bus 18 and/or in series via bus 20.

Optionally, the digital output from micro-processor 10 can be converted to an analog signal. In this instance, the digital output means can comprise digital/analog converter means 22. This ultimately results in an analog output from secondary digital processing circuit 10 via bus 24.

The digital outputs produced by central processing unit micro-processor 10 can be used, for example, for downloading digital information into, or for receiving digital information from, an external source (e.g., a computer). This type of information transfer can be accomplished by any suitable means known to those skilled in the art. Examples of such suitable means include, but are not limited to, the implementation of RS232 and/or RS485 bi-directional digital buses.

Central processing unit 2 is connected to sonde unit 1 via buses 28 and 29. These buses serve as a means for bi-directional digital communication between micro-processor 10 and micro-processor 16. Central processing unit 2 also comprises a power supply 30. This power supply can be provided by any suitable means known in the industry. Examples of such suitable means include, but are not limited to, a dry cell battery, a wet cell battery, a DC converter and/or an AC converter. Power supply 30 is connected, not only to the circuits of central processing unit 2, but also to sonde unit I via line 32.

Sonde unit 1 comprises: (a) a plurality of probes 34 and 36, (b) an electronic selector circuit 38, (c) an input signal acquisition circuit (i.e., A/D converter 40), (d) micro-processor 16 and (e) a source of process operating memory (i.e., ROM 42).

Selector circuit 38 is linked to probes 34 and 36 through lines 44 and 46, respectively. Selector circuit 38 controls the switching between the various electrodes via switching circuits 48 and 50.

Line 54, between selector circuit 38 and microprocessor 16, serves as a means for interrogating selector circuit 38 by central processing unit micro-processor 10 via sonde unit micro-processor 16. This interrogation is carried out by an exchange of digital signals from micro-processor 10 to micro-processor 16, and then to selector circuit 38. Through this interrogation scheme, it is possible to control the following parameters from central processing unit 2: the type of measurement to be carried out, the type of electrode/probe to be used, the nature of the signal from the selected electrode/probe and/or which probe or probes are to be employed.

In practice, probes 34 and 36 are simultaneously monitoring different parameters. The user selects to receive information from one of the probes through the central processing unit micro-processor 10. Microprocessor 10 sends a digital signal to sonde unit micro-processor via line 28, and then to selector circuit 38 via line 54.

The digitalized signal received from micro-processor 16 activates the appropriate switching circuit. This enables an analog signal from one of the probes to pass through line 52 to A/D converter 40, wherein the analog signal is digitalized.

After the analog signal has been digitalized in A/D converter 40, the digital signal is transmitted therefrom to micro-processor 16. Thereafter, the digital signal is transmitted from sonde unit micro-processor 16 to central processing unit micro-processor 10 through line 29.

Once central processing unit micro-processor 10 receives the digitalized signal from sonde unit micro-processor 16, it can process it in many different manners. Examples of manners in which the digitalized signal can be processed include, but are not limited to the following: (a) analyze, display and/or store the information, (b) use the information for recalibration purposes, and/or (c) subject the information to multipass linearization mathematical computations.

After processing the information, central processing unit micro-processor 10 produces digital outputs which can be used as such in parallel or series forms and/or which can be converted to analog signals via optional digital/analog converter means 22.

Regardless of their form, these digital outputs are then transmitted to a digital output means for further processing. Examples of digital output means include, but are not limited to: light emitted diodes (LED) displays, liquid crystal diode (LCD) displays, external computer and/or monitoring sources, a digital/analog converter means, and/or any combination thereof.

Due to the presence of the random access memory storage unit means 12 having the capability of storing at least 500 bytes of information, and the presence of real-time clock means 15, the output from central processing unit micro-processor 10 can be employed as a real-time monitor/alarm and/or for purposes of remote data logging.

Since the analog signals from probes 34 and 36 are digitalized in the sonde unit 1, as opposed to the central processing unit 2, there is no need for sophisticated analog cabling between sonde unit 1 and central processing unit 2. Moreover, since it is much simpler to reproduce a digital signal, as opposed to an analog signal, the degree of digital signal deterioration between sonde unit 1 and central processing unit 2 is negligible.

In view of the above, the multi-probed metering apparatus of the present invention can accurately reproduce monitored parameters over a substantial distance. Moreover, since there is no need for high-priced analog cabling in the metering device of the present invention, this accurate reproduction of monitor parameters can be accomplished at a substantial decrease in cost.

As stated earlier, random access memory storage unit means 12 has the capability of storing at least 500 bytes of information. This enables the metering device of the present invention to make multi-pass linearization mathematical computations.

Although the random access memory storage unit means of the present invention need only handle as low as 500 bytes of information for simple multi-pass linearization mathematical computations, it can be programed to handle between 500 and 5,000,000 bytes of information. If the random access memory storage unit means has the capability of 5,000 and 500,000 bytes of information, it can satisfy most user's needs. In practical applications of monitoring various parameters in aqueous solutions, it is generally preferred that the random access memory storage unit means have the capability of handling between 10,000 and 250,000 bytes of information.

With the presence of a random access memory storage unit means and real-time clock means in central processing unit 2, the multi-probed metering apparatus of the present invention is able to make multi-pass linearization mathematical computations. Moreover, the presence of these components also affords the metering apparatus of the present invention more flexibility since it can perform real-time monitoring/alarming and/or remote data logging.

Another embodiment of the present invention pertains to the multi-probed metering apparatus disclosed herein which further comprises an improved fluid flow-maintaining means. The improved fluid-flow maintaining means of the present invention is integrated into the sonde unit, as opposed to being an external fixture thereon. The fluid-flow maintaining means of the present invention comprises: (a) a stirrer control, (b) a stirrer driving component and (c) a propeller means.

Referring now to FIG. 1, the fluid flow-maintaining means is generally referred to as item 55. Flow-maintaining means 55 comprises stirrer control 56 and stirrer motor 60. Stirrer control 56 is in uni-directional digital communication with sonde unit micro-processor 16 via line 58 and with the stirrer driving component (i.e., stirrer motor 60) via line 62.

Since stirrer control 56 is in uni-directional digital communication with micro-processor 16, which is in turn in bi-directional digital communication with central processing unit micro-processor 10, the flow-maintaining means can be controlled from central processing unit 2. Examples of manners in which the flow-maintaining means can be controlled include, but are not limited to: (a) the direction that the propeller means will rotate (i.e., clockwise and/or counterclockwise), (b) the stirrer R.P.M. can be controlled; (c) the stirrer can be controlled to run intermittently (e.g., run for one minute, then off for one minute) thus conserving energy; and/or (d) the stirrer can be controlled to initially run for a longer period of time and/or at a higher R.P.M. and then go to intermittent running.

Due to the presence of sonde unit micro-processor 16 and stirrer control 56, the fluid flow maintaining means, if employed, can maintain fluid flow over the electrodes/probes of a multi-probed metering apparatus at a reduced cost. Furthermore, since the circuitry for running the flow-maintaining means is within sonde unit 1, the unit can be employed to maintain fluid flow over the electrodes/probes of a multi-probed metering apparatus without subjecting this circuitry to the adverse conditions in which the sonde unit is submerged. Also, since the flow-maintaining means of the present invention can be controlled to run intermittently via central processing unit micro-processor 10 and sonde unit micro-processor 16, the energy consumed, associated with maintaining fluid flow over the electrodes/probes of a multi-probed metering apparatus, can be substantially reduced.

As can be seen, the implementation of the improved fluid flow-maintaining means of the present invention need not be limited to the multi-probed metering apparatus disclosed herein.

Figure 2:
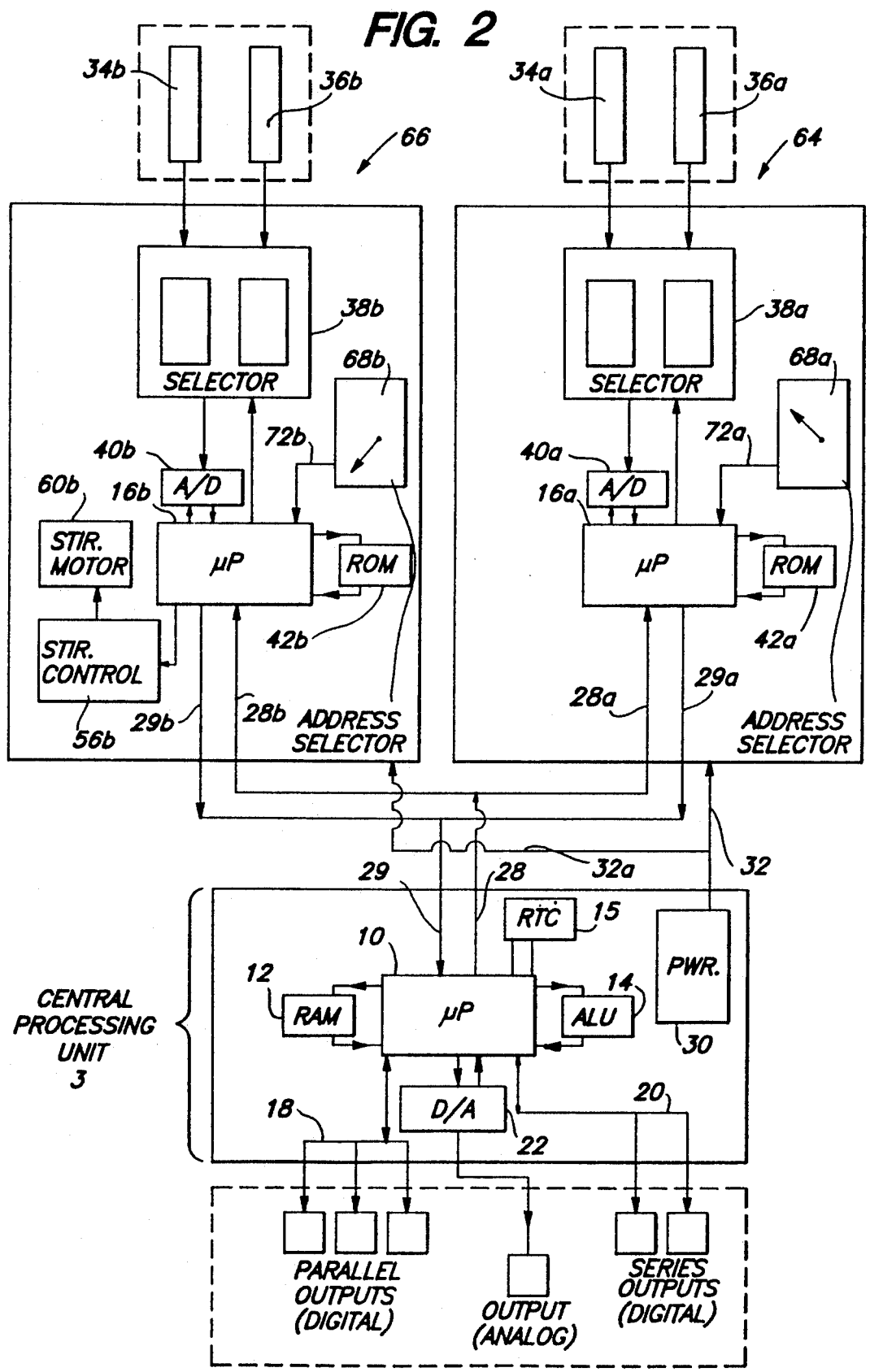
FIG. 2 is an overall schematic circuit diagram of a multi-probed/multi-sonde metering apparatus according to another embodiment of the present invention.

FIG. 2 illustrates another embodiment of a multi-probed metering apparatus encompassed by the present invention. The apparatus illustrated in FIG. 2 comprises one central processing unit generally referred to as item 3 and two separate sonde units generally identified as items 64 and 66. Central processing unit 3 of FIG. 2 comprises all the same components of central processing unit 2 of FIG. 1. Some differences, however, are as follows. First, power supply 30 is connected to sonde unit 64 via line 32 and to sonde unit 66 via line 32a.

As before, micro-processor 10 of the central processing unit is in bi-directional digital communication with the micro-processors of the sonde units. However, since there are two sonde units, micro-processor 10 is in communication with sonde unit 64 micro-processor 16a via lines 28a and 29a, and to said sonde unit 66 micro-processor 16b via lines 28b and 29b.

Sonde unit 66 is identical to sonde unit 1 of FIG. 1 except that sonde unit 66 further comprises address selector 68b.

Address selector 68b is a necessary component in each sonde unit when a plurality of sonde units are controlled by a single central processing unit. Accordingly, sonde unit 64 also comprises an address selector, 68a.

Address selectors 68a and 68b are in uni-directional digital communication with micro-processors 16a and 16b, via lines 72a and 72b, respectively. Simply, address selectors 68a and 68b identify their particular sonde unit. Accordingly, if the user wishes to see a measurement from one of the electrodes in sonde 66, address selector 68b would inform micro-processor 16b that its electrodes are being selected. Similarly, address selector 68a would inform micro-processor 16a that its electrodes are not being selected. These micro-processors then instruct their respective selector circuits (i.e., selector circuits 38b and 38a) to act accordingly. By the presence of micro-processors 16a and 16b within their respective sonde units, then the cabling necessary for address selectors 68a and 68b to perform their function is minimized.

The remainder of the components and their respective functions in sonde units 64 and 66 are identical to those in sonde unit 1 of FIG. 1. As can also be seen, sonde unit 64 does not include the optional fluid flow-maintaining means of the present invention.

Figure 3:
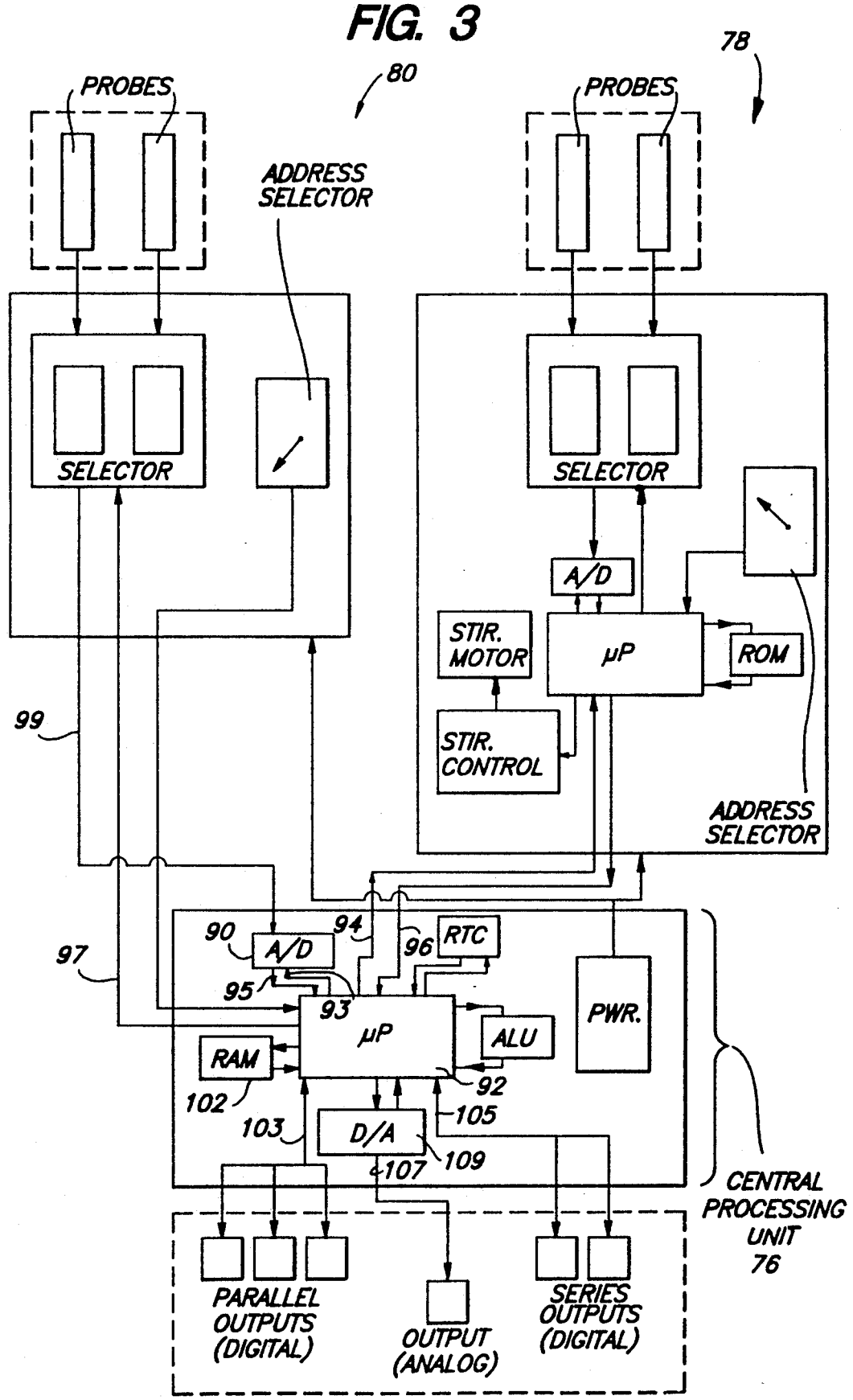
FIG. 3 is an overall schematic circuit diagram of a multi-probed/multi-sonde metering apparatus according to still another embodiment of the present invention.

Yet another embodiment of a multi-probed metering apparatus encompassed by the present invention is illustrated in FIG. 3. The multi-probed metering apparatus illustrated in FIG. 3 comprises a central processing unit generally referred to as item 76, and two sonde units, generally referred to as items 78 and 80.

Except for the presence of the improved flow-maintaining means in sonde unit 78, sonde unit 78 comprises the same components as those illustrated in sonde unit 64 of FIG. 2. On the other hand, while sonde unit 80 does comprise probes, an electronic selector circuit and an address selector, it does not comprise an operating memory unit (i.e., a ROM unit), an analog/digital converter means or a micro-processor.

In view of the above, central processing unit 76 has been slightly modified for signal conditioning of such types of electrodes, thus expanding even more the flexibility of the novel metering apparatus of the present invention. Generally, central processing unit 76 further comprises additional circuitry to compensate for the components omitted from sonde unit 80. For example, in addition to the components present in central processing units 2 and 3 of FIGS. 1 and 2, respectively, central processing unit 76 further comprises an analog/digital converter means 90 which is in bi-directional digital communication with central processing unit micro-processor 92 via lines 93 and 95. Analog/digital converter 90 is also in uni-directional digital communication with sonde unit 80 electronic selector circuit. Moreover, since there is no micro-processor in sonde unit 80, its electronic selector circuit and address selector are both in uni-directional digital communication with central processing unit micro-processor 92.

In practice, if a user desires to monitor a signal from sonde unit 78, micro-processor 92 would interrogate the signals from the address selectors of each sonde unit. Based upon this interrogation scheme, it will transmit a digital signal to the micro-processor of sonde unit 78 via line 94. The micro-processor of sonde unit 78 will then transmit a digital signal to the electronic selector circuit of that same sonde unit.

The selected monitored analog signal from the electrode/probes in sonde unit 78 will then pass through the electronic selector circuit to the A/D converter means, wherein the analog signal will be digitalized.

Thereafter, the digital signal will pass to central processing unit micro-processor 92 via sonde unit 78 micro-processor and line 96. Central processing unit micro-processor 92 will then process the signal according to the user's desire.

On the other hand, if the user desires to monitor a signal from sonde unit 80, micro-processor 92 would again interrogate the signals from the address selectors of each sonde unit. Based upon this interrogation scheme, micro-processor 92 will transmit a digital signal to the electronic selector circuit of sonde unit 80 via line 97.

The selected monitored analog signals from the electrodes/probes in sonde unit 80 will then pass through the electronic selector circuit of sonde unit 80 to A/D converter means 90 in central processing unit 76 via line 99. The analog signals will then be digitalized.

Thereafter, the digital signal will pass from A/D converter means 90 to micro-processor 92 via line 95. Central processing unit micro-processor 92 will then process the signal according to the user's desire.

Due to the enlarged storage capabilities of central processing unit 76 random access memory storage unit means (i.e., RAM 102), information from sonde units 78 and 80 can be employed to perform multi-pass linearization mathematical computations in micro-processor 92.

As stated before, after these mathematical computations have been made, micro-processor 92 produces a digital output relating thereto. This digital output can be used as such in parallel form along bus 103, in series form along bus 105 and/or in analog form along line 107, after first passing through digital/analog converter means 109.

As can be seen, the circuitry and design of the improved multi-probed metering apparatus of the present invention affords a user a degree of flexibility which has, heretofore, not been provided by a self-sustained hand-held multi-probed unit. Examples of the increased degree of flexibility afforded by the improved multi-probed metering apparatus of the present invention include, but are not limited to:

(a) Up to 32 channels can be configured, for example, for: sensor-type, input signal type, engineering symbol, and linearization. These can be user-selected through the improved multi-probed metering apparatus of the present invention without having to be interfaced with a external computer source.

(b) The improved metering apparatus of the present invention can be either completely programmed without being connected to an external computer source, or programmed via external computer software or both. Specifically, due to the circuitry design of the present invention, the improved metering apparatus of the present invention has the capability of having a central processing unit with a full-functioning menu. This allows the user to change various parameters while in the field without having to interface the apparatus with an external computer source.

(c) The central processing unit micro-processor can either use its own signal conditioning circuit (e.g., an A/D converter means) to measure signals directly and calculate the resultant display, or can communicate, via a bi-directional digital bus to a signal conditioning circuit in the sound unit, or both (see, for example, FIG. 3).

(d) The central processing unit of the multi-probed apparatus of the present invention has the capability of storing data in its own random access memory storage unit means (i.e., RAM), or outputting the data as it makes the measurement through its digital output lines, or both.

(e) The central processing unit of the multi-probed metering apparatus of the present invention can have its digital output connected to an external computer source, as stated earlier, or to a printer. This feature eliminates the need to employ a computer when requiring only a printout of results.

In addition to the above, the flexibility of the improved multi-probed metering apparatus of the present invention also affords it the ability to be employed in a number of different configurations. Examples of such possible configurations include, but are not limited to:

(a) A plurality of sonde units can be connected to a multiplexing box which then connects to a single central processing unit. This allows one central processing unit to program and control a plurality of sonde units (see, for example, FIG. 2).

(b) Since the central processing unit of the multi-probed metering apparatus of the present invention can be designed to include its own signal conditioning circuit (i.e., its own A/D converter means), one central processing unit can receive and process signals from both digital output-producing sonde units and analog output-producing sonde units (see. for example, FIG. 3).

(c) The improved multi-probed metering apparatus of the present invention can have the digital output produced by its central processing unit micro-processor used to set alarm conditions and/or to report results in real time, while simultaneously data logging. This feature is especially useful when monitoring alarm levels at dangerous chemical concentrations. This real time reporting and alarm monitoring can occur simultaneously with the in-field data logging capabilities. It is also possible to record data only when an alarm situation has occurred.

A further embodiment of the present invention comprises the implementation of a novel fluid flowing-maintaining means in conjunction with the above-described multi-probed metering apparatus. The improved fluid flow-maintaining means of the present invention is integrated into the body of the sonde unit, as opposed to being an external fixture thereon.

To skilled artisans, it would be undesirable to integrate a flow-maintaining means within the body of the sonde unit due to the necessity at the sonde unit to have a water-tight seal within the sonde. Therefore, as stated earlier, conventional flow-maintaining means are typically attached to the external body of the sonde unit thus eliminating any problems associated with destroying the water-tight configuration of the sonde unit.

The embodiment of the present invention pertaining to an improved flow-maintaining means for multi-probed metering apparatuses integrates the flow-maintaining means within the body of the sonde unit. This integration is accomplished without destroying the water-tight configuration of the sonde unit.

Figure 4:
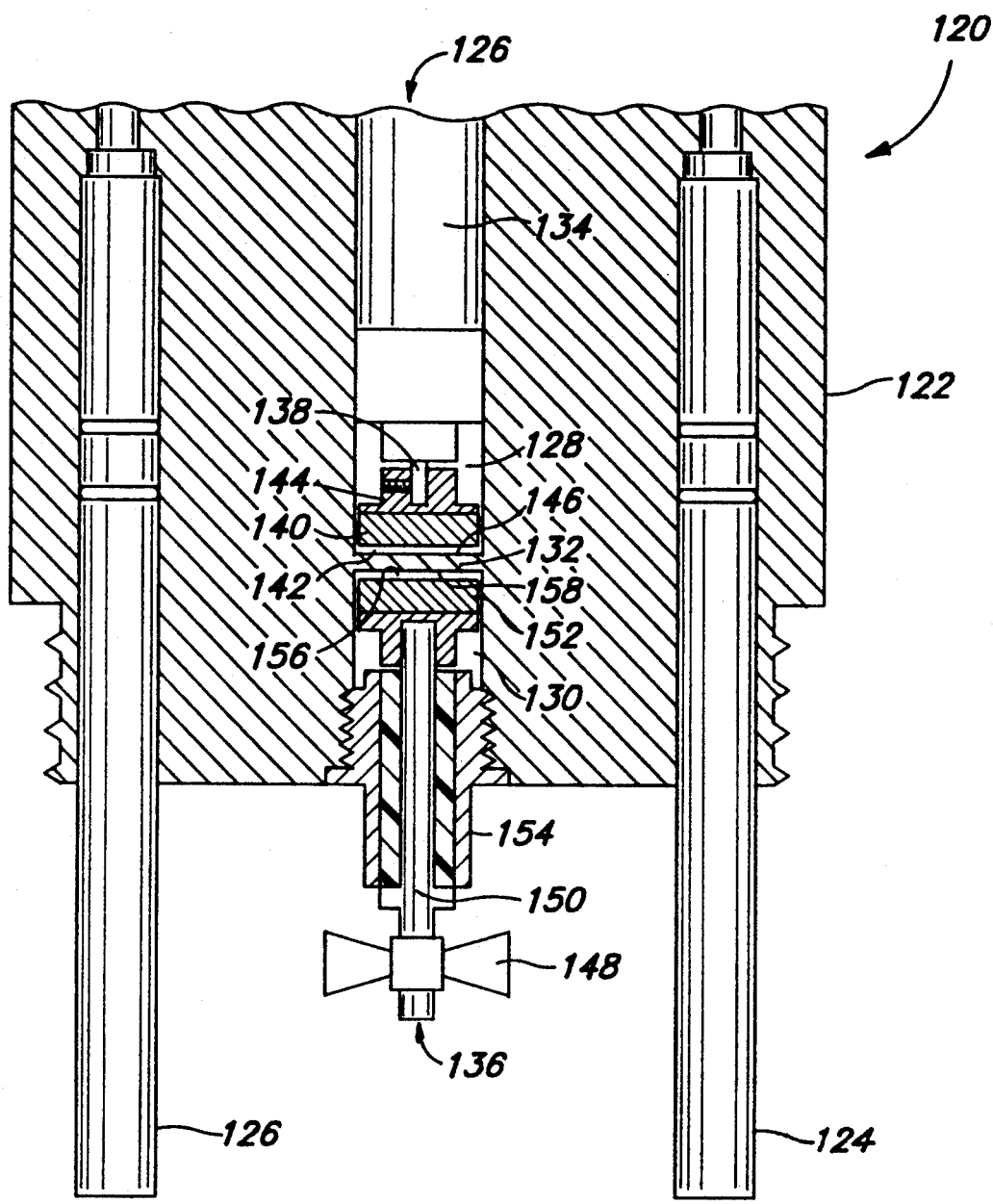
FIG. 4 is a partial side cross-sectional view of sonde unit with an improved fluid flow-maintaining for a multi-probed metering apparatus.

FIG. 4 illustrates one embodiment of an improved flow-maintaining means in accordance with the present invention. Specifically, FIG. 4 is a side, partial cross-sectional view of the monitoring portion of a sonde unit comprising one embodiment of an improved fluid flow-maintaining means.

In FIG. 4, the sonde unit is generally referred to as item 120. Sonde unit 120 comprises: sonde body 122, probes 124 and 126, and improved fluid flow-maintaining means generally referred to as item 126.

For purposes of having flow-maintaining means 126 integrated into sonde body 122, two opposing and aligned chambers 128 and 130 are defined in sonde body 122. These chambers define a sonde body wall portion 132 therebetween. Moreover, there is no physical passage between chambers 128 and 130.

Flow-maintaining means 126 comprises: stirrer driving component 134 and propeller component 136. Drive component 134 comprises: a rotating means (not shown) for turning an object in a clockwise or counterclockwise manner (e.g., a motor), a drive component shaft 138 and a magnet means 140. Drive component shaft 138 interconnects magnet means 140 to rotating means.

Magnet means 140 has at least one planar surface 142 which is generally perpendicular to the longitudinal axis of drive component shaft 138. Magnet means 140 also comprises an attaching means 144 for physically connecting magnet means 140 to drive component shaft 138.

Drive component 134 is dimensioned such that it can fit into chamber 128 defined in sonde body 122. Drive component 134 also comprises a means (not shown) for fixedly connecting it to sonde body 122.

The overall length and configurations of the drive component 134 is such that, when it is inserted into chamber 128, and fixedly attached to sonde body 122, magnet means 140 is in close adjacent relationship with the upper surface 146 of sonde body wall portion 132. Moreover, the overall length and configuration of drive component 134 should be such that, when drive component 134 is positioned into sonde chamber 128 and fixedly attached to sonde body 122, magnet means 140 can freely rotate in a clockwise or counterclockwise direction.

Flow-maintaining means propeller component 136 comprises: propeller means 148, shaft 150, magnet means 152 and securing means 154. Magnet means 152 is physically connected to propeller means 148 via shaft 150. This configuration is, in turn, rotatably attached to securing means 154. Magnet means 150 comprises at least one planar surface 156 having a longitudinal axis which is generally perpendicular to that of shaft 150.

Propeller component 136 is dimensioned such that it can be fixedly attached to sonde body 122 and fit within sonde body chamber 130. Specifically, propeller component 136 should be dimensioned such that, when fixedly attaching securing means 154 to sonde body 122, the magnet means at least one planar surface 156 is in close adjacent relationship with the lower surface 158 of sonde body wall portion 132. After propeller component 136 is fixedly attached to sonde body 122, magnet means 152 must be able to freely rotate within chamber 130 in a clockwise or counterclockwise direction.

The magnetic fields emitted by magnet means 140 and 152 must be sufficient to pass through sonde body wall portion 132 and magnetically connect magnet means 140 with magnet means 152.

In practice, drive component 134 and propeller component 136 are fixedly attached to sonde body 122. Drive component 134 then rotates magnet means 140 in either a clockwise or counterclockwise direction. Since the magnetic fields emitted by magnet means 140 and 152 are sufficient to pass through sonde body wall portion 132 and magnetically connect the magnets together, by rotating magnet means 140, a corresponding rotation will occur with magnet means 152. This, in turn, will cause propeller means 148 to rotate, thus, causing fluid to flow over probes 124 and 126.

Since there is no physical connection between drive component 134 and propeller component 136, flow-maintaining means 136 is integrated into sonde body 122 without destroying the sonde body water-tight configuration. Furthermore, due to the integration of flow-maintaining means 126 into sonde body 122, the overall size of sonde unit 120 is substantially reduced.

While the improved flow-maintaining means of the present invention is especially useful with the improved multi-probed metering apparatus disclosed herein, it is not necessarily limited thereto.

As stated earlier, another problem associated with many of the conventional multi-probed metering apparatuses pertains partially to repairing and/or replacing damaged electrodes/probes, and partially to changing the parameters which the electrode/probes monitor. As noted above, since many of the conventional multi-probed metering apparatuses are employed to measure various parameters in fluids (e.g., water), the connection between the electrodes/probes and the circuitry within the sonde unit must remain dry. Therefore, as stated above, the sonde unit must have a water-tight configuration.

Due to the above, if particular electrodes/probes have to be repaired or replaced for one reason or another, this generally means that the entire sonde unit has to be taken out of commission and returned to a shop where this work can be performed. Since maintaining an inventory of spare sonde parts is a very costly endeavor, the industry would welcome a device which enables, and/or has means for, field replacement and/or repair of electrodes/probes, without destroying the necessary, water-tight configuration of the sonde unit.

Accordingly, yet a further embodiment of the present invention pertains to a means for field replacement and/or repair of electrodes/probes of the multi-probed metering apparatus disclosed herein, without destroying the water-tight configuration of the sonde unit. One example of such a means encompassed by this embodiment of the present invention is illustrated in FIG. 5.

Figure 5:
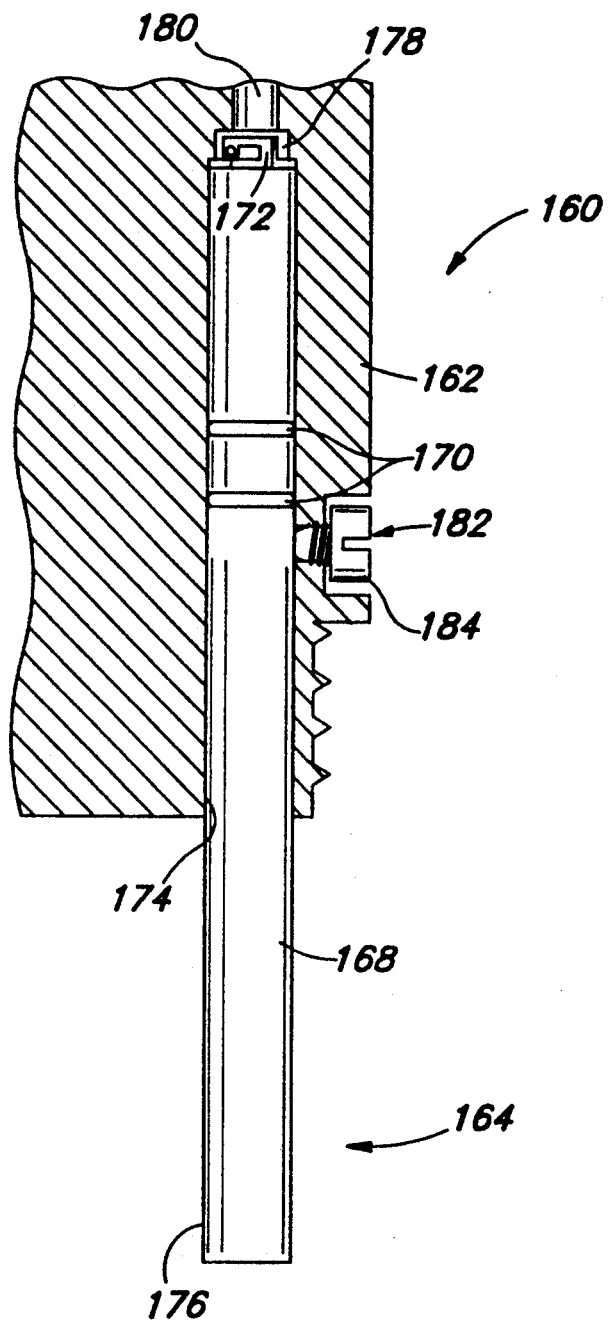
FIG. 5 is a partial side cross-sectional view of a sonde unit with means for field repairing and/or replacing electrodes/probes of a multi-probed metering apparatus.

FIG. 5 is a partial side cross-sectional view of a sonde unit with one embodiment of a means for field replacing and/or repairing electrodes/probes without destroying a water-tight configuration. In FIG. 5, the sonde unit is generally referred to as item 160. Sonde unit 160 comprises: sonde body 162, and monitoring component generally referred to as item 164.

Monitoring component 164 comprises: probe 168, sealing means 170 and connecting means 172. Sonde body 162 has a probe-receptacle chamber defined therein. This chamber, in turn, defines sonde body inside wall surface 174.

Monitoring means component 164 is dimensioned such that the probe outside wall surface 176 is in close abutting or adjacent relationship with the sonde unit inside wall surface 174. Sealing means 170 is comprised of a deformable material. The circumference of sealing means is slightly larger than that of the sonde body chamber defined by inside wall surface 174 such that a water-tight seal between is made. This is typically termed an O-ring.

This embodiment of the present invention requires a coupling means 178, signal cable 180 and monitoring component 164. In the embodiment illustrated in FIG. 5, coupling means 178 is a conventional BNC socket. Coupling means 178 is designed to accept connecting means 172 of probe 168.

The coupling means of this embodiment can be any such suitable means known to those skilled in the art. Examples of other suitable coupling means include, but are not limited to, DIN connectors and/or coaxial connectors.

In practice, if there is a need to replace and/or repair an electrode/probe in accordance with this embodiment of the present invention, probe 168 is manuevered to disengage connecting means 172 from coupling means 178. Thereafter, probe 168 is retracted from the sonde body chamber defined by inside wall surface 174.

The replacement monitoring component 164' (not shown) is then introduced into the sonde body chamber defined by inside wall surface 174. Thereafter, this monitoring component's connecting means 172' (not shown) would be engaged with coupling means 178.

Due to the presence and configuration of sealing means 170, this method of replacing probes in a sonde unit does not destroy the sonde unit's necessary water-tight configuration. Specifically, the deformable nature of sealing means 170 causes the sealing means to press tightly against the sonde body inside wall surface 174, thus creating a water-tight seal. The size, composition and shape of the sealing means employed in this embodiment of the invention depends upon: (a) the composition of the solution in which the sonde is being submerged, (b) the amount of pressure exerted by the solution into which the sonde is being submerged, and/or (c) the temperature of the solution into which the sonde is being submerged.

Optionally, a means can be employed to secure monitoring component 164 to sonde body 162. Any such suitable means known to those skilled in the art can be employed. The securing means must not, however, destroy the water-tight configuration of the sonde unit.

In the embodiment illustrated in FIG. 5, the optional securing means comprises a grub screw configuration generally referred to as item 182. This grub screw configuration comprises grub screw 184 and a corresponding threaded portion within sonde body 162. This corresponding threaded portion is generally perpendicular to the longitudinal axis of the sonde body chamber defined by wall surface 174, and opens into the sonde body chamber. In practice, the monitoring portion 164 is first engaged into the sonde body chamber by coupling means 178. Thereafter, grub screw 184 is threaded into sonde body 162 until grub screw 184 contacts probe outside wall surface 176 and causes probe outside wall surface 176 to press against the sonde body inside wall surface 174.

It should be noted that, since the securing means illustrated in FIG. 5 requires a passageway from outside the sonde body to a chamber within the sonde body, this particular embodiment of a securing means must be positioned below sealing means 170. To do otherwise would destroy the necessary sonde body water-tight configuration.

Still a further embodiment of the present invention pertains to the multi-probe metering apparatus disclosed herein which further comprises an improved means for calibrating its plurality of electrodes/probes. One embodiment of this improved calibration means is illustrated in FIGS. 6-9.

Figure 6:
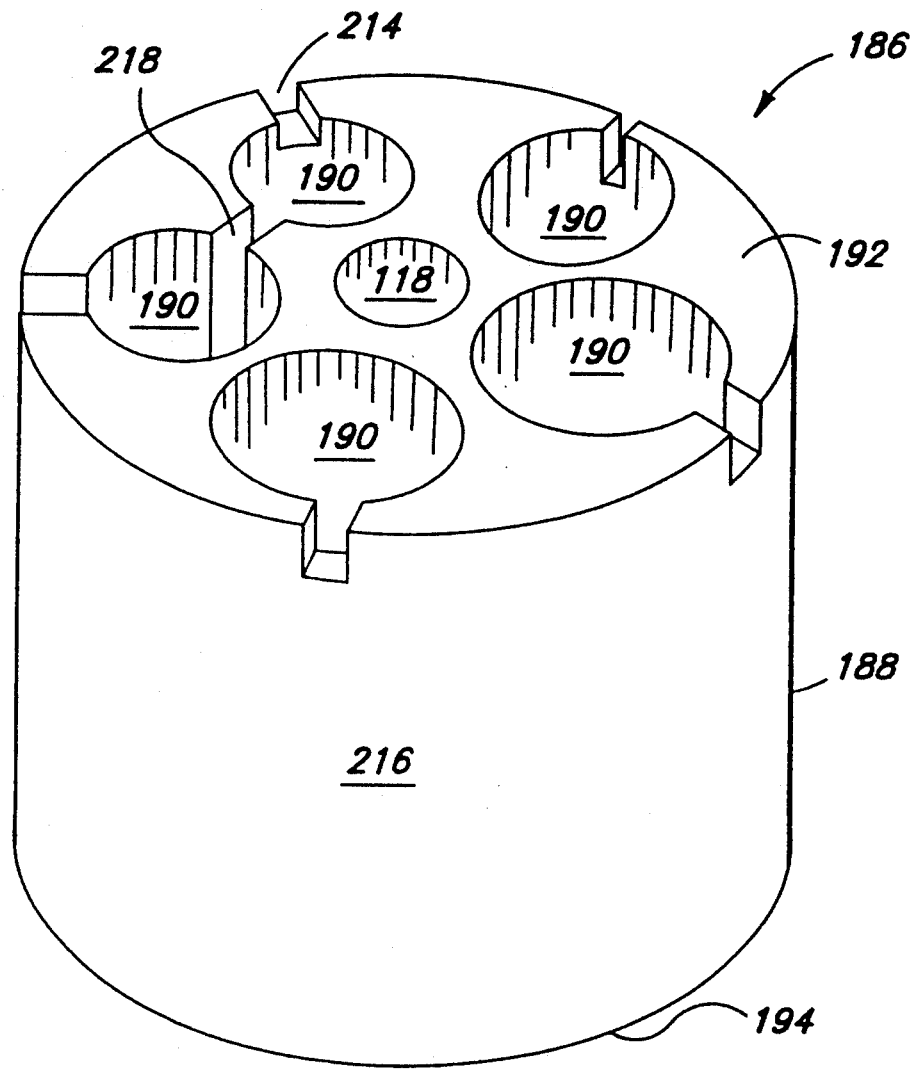
FIG. 6 is an elevation view of one embodiment of an improved calibration means of a multi-probed metering apparatus in accordance with a further embodiment of the present invention.
Figure 7:
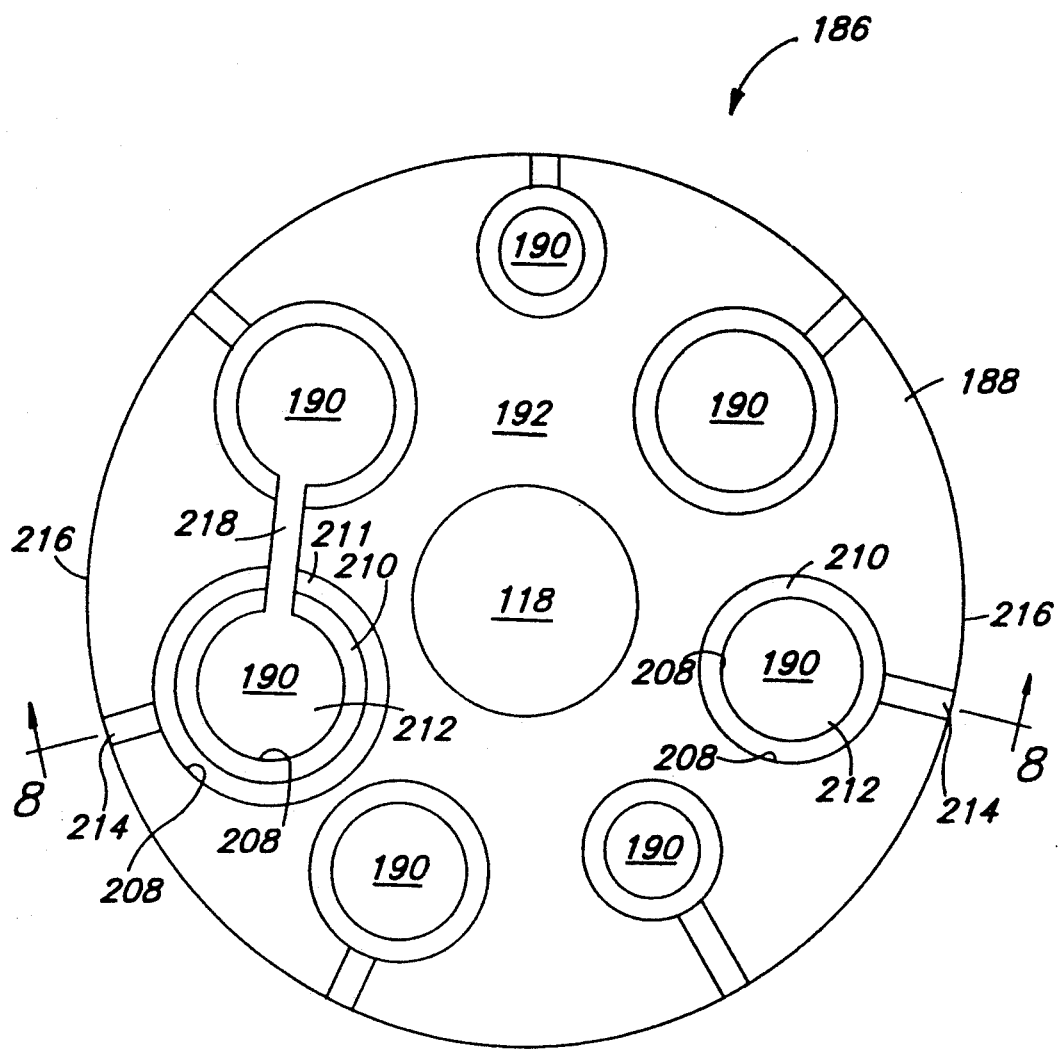
FIG. 7 is a top view of one embodiment of an improved calibration means for a multi-probed metering apparatus in accordance with the present invention.
Figure 8:
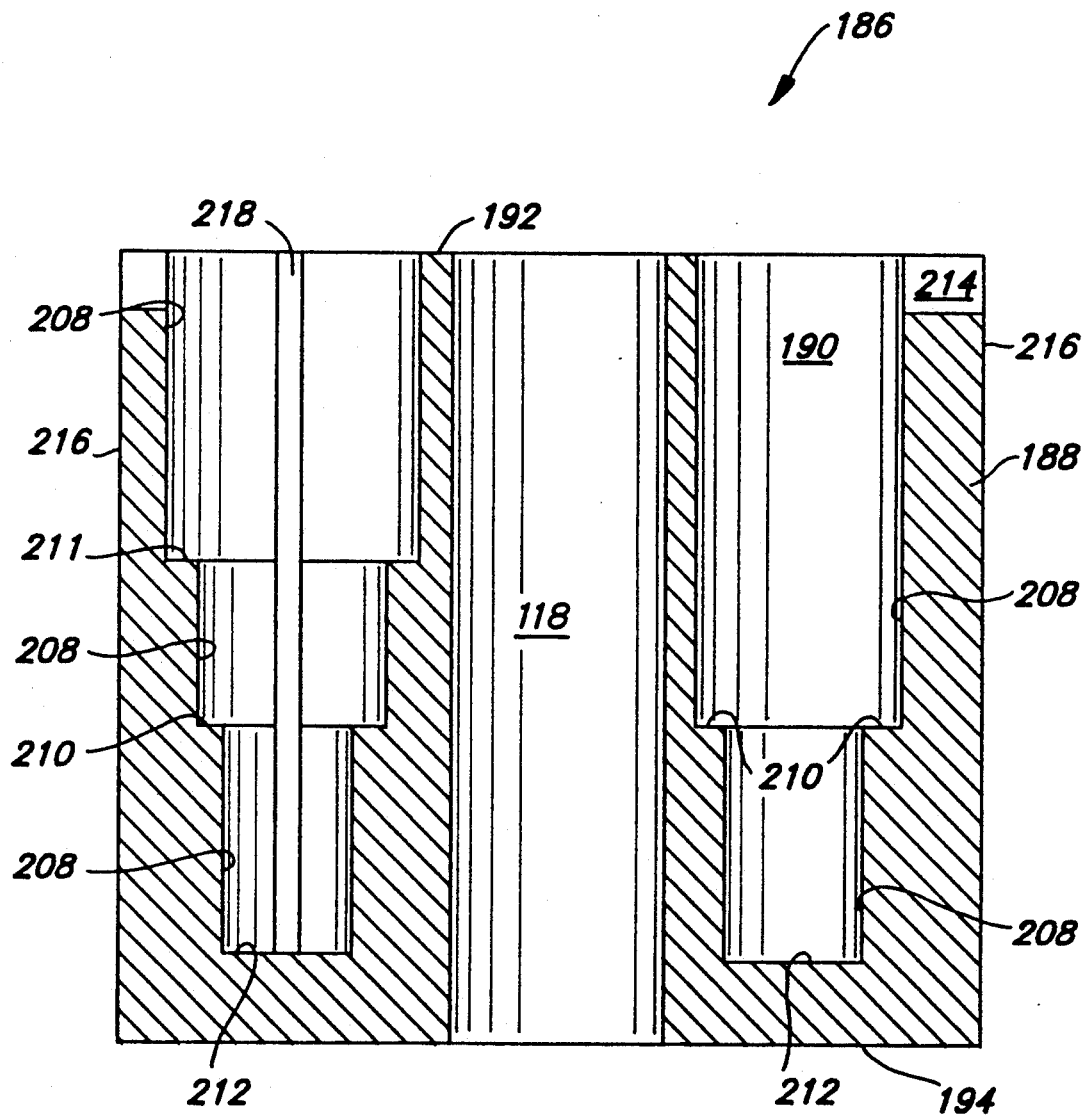
FIG. 8 is a side cross-sectional view of the improved calibration means for a multi-probed metering apparatus illustrated in FIG. 7, taken along line 8—8.
Figure 9:
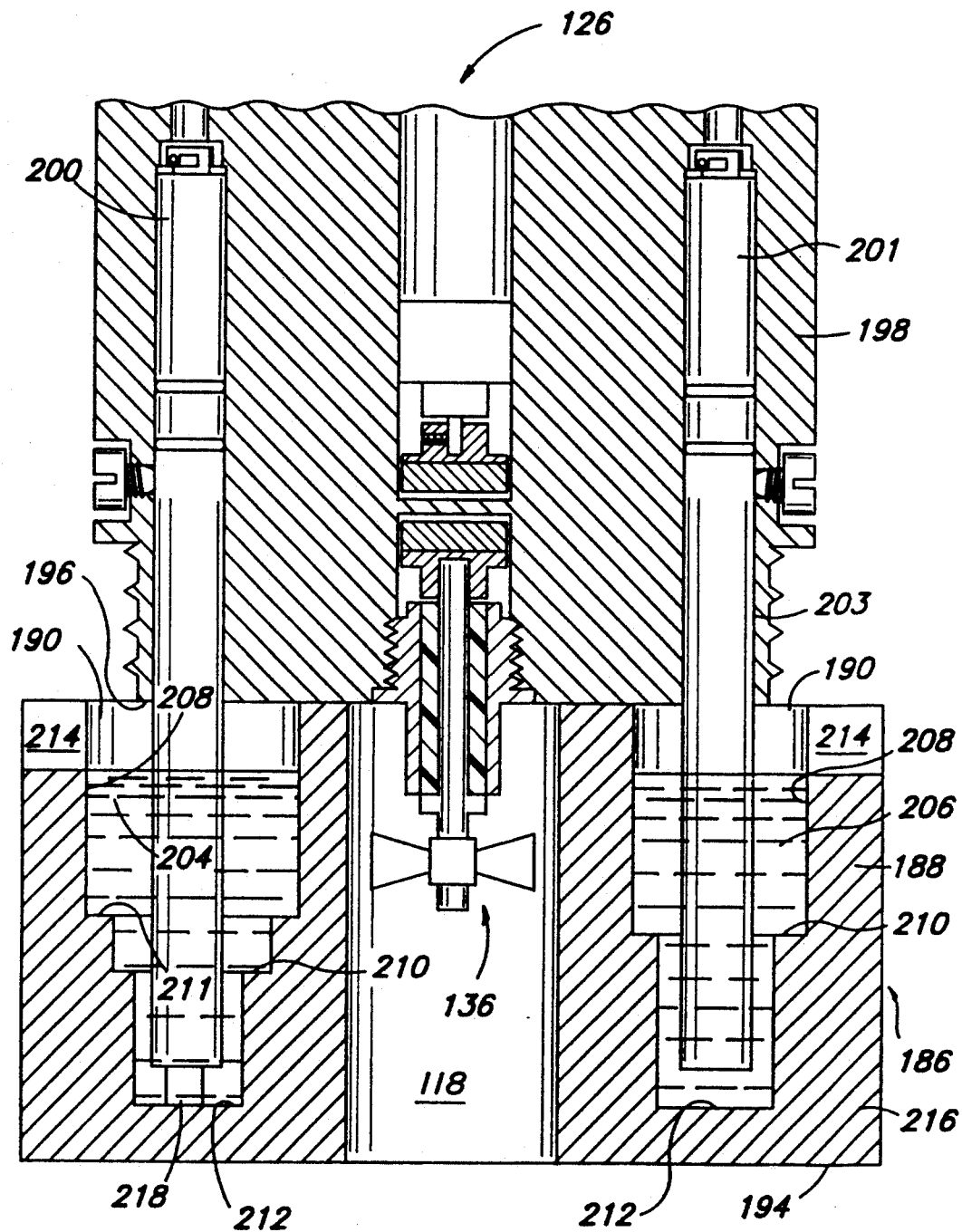
FIG. 9 is a partial side cross-sectional view of a sonde unit with an improved fluid flow-maintaining means and an improved calibration means for a multi-probed metering apparatus.

FIG. 6 is an elevation view of one embodiment of an improved calibration means for a multi-probe metering apparatus in accordance with the present invention. FIG. 7 is a top view of one embodiment of an improved calibration means. FIG. 8 is a side-cross sectional view of the improved calibration means illustrated in FIG. 7, taken along line 8—8. FIG. 9 is a partial side cross-sectional view of a sonde unit comprising, among other things, an embodiment of an improved calibration means in accordance with the present invention.

In FIGS. 6-9, the improved calibration means is generally referred to as item 186. Calibration means 186 comprises a polyhedrally-shaped calibration cup body 188 having at least two parallel planar surfaces 192 and 194.

Cup body 188 has a plurality of vertically-oriented calibration wells 190 defined therein. Wells 190 pass through cup body upper surface 192. They do not, however, pass through cup body lower surface 194 (shown only in FIGS. 6, 8 and 9).

The configuration of wells 190 in cup body 188 correspond with the configuration of electrode/probes protruding from the lower portion 196 of a particular sonde body 198 (shown only in FIG. 9). The depth of wells 190 must be greater than the length of the electrode/probe which extends from the lower surface 196 of sonde body 198 (Only shown in FIG. 9).

Therefore, in practice, probes 200 and 201 must be able to fit within corresponding wells 190 in cup body 188 such that the sonde body lower portion 196 rests against cup body upper surface 192 as illustrated in FIG. 9. In addition, the configuration of wells 190 must be such that, when probes 200 and 201 are inserted into their corresponding wells, there is a space between the probes' outer wall surface 203 and the cup inside wall surface 208.

When employing the improved calibration means of the present invention to calibrate the plurality of electrodes/probes of a multiprobed device, calibration solutions 204 and 206 are poured into wells 190 which correspond with the electrodes/probes with which the particular solution pertains. For example, if probe 200 monitors pH and probe 201 monitors turbidity, solution 204 would be a pH calibration solution and solution 206 would be a turbidity calibration solution.

After each well is filled to the appropriate level with the proper calibration solution, the electrodes/probes are positioned over their corresponding wells, and are inserted therein until the sonde body lower surface 196 rests upon calibration cup upper surface 192. This will result in each electrode/probe being at least partially surrounded with its particular calibration solution. Thereafter, each probe is calibrated accordingly.

As can be seen, the improved calibration means of the present invention significantly reduces calibration time, when compared to conventional calibration techniques. Moreover, this improved calibration technique also eliminates the possibility of contaminating one particular electrode/probe with the calibration solution for another electrode/probe.

The improved calibration means of the present invention can also, optionally, comprise a means for determining the appropriate amount of calibration solution which should be introduced into the well, prior to insertion of the electrodes/probes therein. Any suitable technique can be employed for this practice. For example, markings can be placed on the inside wall surface of the wells. Another method comprises fabricating the cup body out of a transparent or translucent material. Yet a another method comprises the addition of a premeasured amount of calibration solution within the well.

One method which the inventor has found particularly useful, inexpensive, and simple to implement is illustrated in FIGS. 7-9. As can be seen, the vertically-oriented inside wall surfaces 208 of wells 190 have horizontally-oriented ledges 210 formed therein.

The distance between ledge 210 and well bottom surface 212 is such that, when a calibrating solution is filled to ledge 210, inserting the respective probe within well 190 would not result in the calibration solution pouring over cup body upper surface 192. The positioning of ledge 210 within well 90 must take into consideration the total volumetric capacity of well 190 and the amount of solution which will be displaced by that portion of the probe submerged within the calibrating solution.

In certain instances an electrode/probe has to be calibrated for two different parameters (e.g., zero setting and slope setting).

Certain electrodes/probes may require that they are electrically connected to one another during calibration. An example would be the measurement of sodium and contact with a pH electrode. In this case, a slot 218 (FIGS. 6-9) is present between two separate calibration wells. This slot allows the fluid to flow between the two wells. Additionally, the required volume of calibrating a specific parameter of each sonde unit may be different. Therefore, the improved calibration means of the present invention can be modified to include a second ledge 211 defined within well 190. An example of this modification to the improved calibration means of the present invention is illustrated in FIGS. 7-9.

Another means for preventing the contamination of a particular electrode/probe with the calibration solution of a different electrode/probe comprises the implementation of an overflow channel defined in the cup body upper surface. This method of preventing cross contamination is illustrated in FIGS. 7-9.

In FIGS. 7-9, the overflow channel is referred to as item 214. Overflow channel 214 passes from cup body outside wall surface to 216 to cup body inside wall surface 208.

In practice, the combined volume of calibration solution present within well 190 and the portion of the electrode/probe submerged within the calibration solution is greater than the total volumetric capacity of well 190, the excess amount of calibration solution will escape from well 190 through channel 214. This technique insures that specific probes will not be contaminated by a calibration solution from one well overflowing into an adjacent well.

In the embodiment of the improved calibration means illustrated in FIGS. 6-9, an opening 118 is also defined within cup body upper surface 192. This opening is dimensioned to receive propeller portion 136 of fluid flow-maintaining means 126. Opening 218 can pass completely through cup body 188. However, this is not necessary.

As indicated earlier, the implementation of the improved fluid flow-maintaining means is an optional feature of the present invention. Accordingly, opening 118 is also optional.

As can be seen, the improved calibration means of the present invention can reduce calibration times for multi-probed metering apparatuses by over 50%. Moreover, as can also be seen, the improved calibration means of the present invention need not be limited to the specific multi-probe metering apparatus disclosed herein.

It is evident from the foregoing that various modifications can be made to embodiments of this invention without departing from the spirit and scope thereof, which will be apparent to those skilled in the art.

That which is claimed is:

1. A multi-probed metering apparatus for measuring electrical magnitudes comprising:
   (a) at least one sonde unit, wherein said sonde unit comprises:
      (i) a plurality of pick-up means,
      (ii) an analog/digital converter means,
      (iii) a selector circuit for identifying each of said plurality of pick-up means with which said sonde unit is associated, said selector circuit interfaces said plurality of pick-up means with said analog/digital converter means,
      (iv) primary digital signal processing circuit, said primary digital signal processing circuit being in bi-directional digital communication with said analog/digital converter means and in uni-directional digital communication with said selector circuit, and
      (v) an improved fluid flow-maintaining means, said fluid flow-maintaining means comprising: stirrer control, stirrer driving component, and propeller component interconnected with said stirrer driving component, said stirrer control being in uni-directional digital communication with said sonde unit primary digital signal processing and with said stirrer driving component; and
   (b) a central processing unit, wherein said central processing unit comprises:
      (i) a power supply for said central processing unit and said sonde unit,
      (ii) a real-time clock means,
      (iii) a random access memory storage unit means for handling at least 500 bytes of information,
      (iv) an arithmetic and logic unit means for making multi-pass linearization mathematical computations,
      (v) a digital output means,
      (vi) a secondary digital signal processing circuit supplying a digital output, said secondary digital signal processing circuit being in bi-directional digital communication with said sonde unit primary digital signal processing circuit, said real-time clock means, said random access memory storage unit means, said arithmetic and logic unit means, and said digital output means, and
      (vii) means for processing said digital output from said secondary signal processing circuit.

2. A multi-probed metering apparatus as in claim 1 wherein said stirrer control controls said stirrer driving component to perform at least one of the following functions:
   (a) the direction that said propeller means will rotate,
   (b) the revolutions per minute which said propeller means will rotate, and/or (c) intermittent rotating of said propeller means.

3. A multi-probed metering apparatus as in claim 1,
   (a) wherein said stirrer driving component comprises:
      (i) magnet means, said magnet means having at least one planar surface,
      (ii) rotating means for turning said magnet means in a clockwise or counterclockwise direction, and
      (iii) shaft means, said shaft means longitudinal axis being generally perpendicular to said magnet means at least one planar surface, and said shaft means interconnecting said magnet means and said rotating means, and
   (b) wherein said propeller component comprises:
      (i) propeller means for creating a fluid flow,
      (ii) magnet means, said propeller component magnet means having at least one planar surface, and
      (iii) shaft means, said propeller component shaft means longitudinal axis being generally perpendicular to said propeller component magnet means at least one planar surface, and said propeller component shaft means interconnecting said propeller component magnet means and said propeller means,
   said stirrer driving component magnet means planar surface being in alignment with, but spaced apart from, said propeller component magnet means planar surface, and said stirrer driving component magnet means being magnetically interconnected with said propeller component magnet means.

4. A multi-probed metering apparatus as in claim 1, further comprising a means for calibrating said pick-up means, wherein said calibration means comprises a polyhedrally-shaped calibration cup body having at least two parallel planar surfaces, said calibration body defines a plurality of vertically-oriented calibration wells which, while passing through one of said at least two parallel planar surfaces, do not pass through the opposing parallel planar surface, the configuration of the openings in the calibration cup body parallel planar surface through which the calibration wells pass corresponds with the configuration of said plurality of pick-up means in said sonde unit, and said calibration wells being dimensioned such that, when said plurality of pick-up means are introduced therein, the outside wall surfaces of said pick-up means within said calibration wells are spaced apart from said calibration cup body inside wall surfaces defined by said calibration wells.

5. A multi-probed metering apparatus as in claim 4 further comprising a means for measuring the amount of calibration fluid which should be introduced therein.

6. A multi-probed metering apparatus as in claim 4 further comprising a means for preventing cross-contamination of one of said plurality of pick-up means by a calibration solution of another of said plurality of pick-up means.

7. A multi-probed metering apparatus as in claim 4 further comprising a means for fluidly interconnecting a plurality of said calibration wells together.

8. A multi-probed metering apparatus as in claim 4 further defining a well configured and dimensioned to accept said fluid-flow maintaining means.

9. A multi-probed metering apparatus as in claim 1 wherein at least one of said plurality of pick-up means comprises:
   (a) a monitoring end portion,
   (b) a signal transmitting end portion, said signal transmitting end portion comprising a means for interconnecting said pick-up means to said sonde unit, and
   (c) sealing means located between said monitoring end portion and said signal transmitting end portion, said sealing means being dimensioned to prevent the flow of fluid between said pick-up means monitoring end portion and said pick-up means signal transmitting end portion.

10. A multi-probed metering apparatus as in claim 9 wherein said at least one of said plurality of pick-up means further comprises means for securing said at least one of said plurality of pick-up means to said sonde unit, said securing means being positioned between said pick-up means monitoring end portion and said sealing means.

11. A multi-probed metering apparatus for measuring electrical magnitudes comprising:
   (a) at least one sonde unit, wherein said sonde unit comprises:
      (i) a plurality of pick-up means,
      (ii) an analog/digital converter means,
      (iii) a selector circuit for identifying each of said plurality of pick-up means with which said sonde unit is associated, said selector circuit interfaces said plurality of pick-up means with said analog/digital converter means,
      (iv) primary digital signal processing circuit, said primary digital signal processing circuit being in bi-directional digital communication with said analog/digital converter means and in uni-directional digital communication with said selector circuit, and
      (v) an address selector which identifies said at least one sonde, said address selector being in uni-directional digital communication with said sonde unit primary digital signal processing circuit; and
   (b) a central processing unit, wherein said central processing unit comprises:
      (i) a power supply for said central processing unit and said sonde unit,
      (ii) a real-time clock means,
      (iii) a random access memory storage unit means for handling at least 500 bytes of information,
      (iv) an arithmetic and logic unit means for making multi-pass linearization mathematical computations,
      (v) a digital output means,
      (vi) a secondary digital signal processing circuit supplying a digital output, said secondary digital signal processing circuit being in bi-directional digital communication with said sonde unit primary digital signal processing circuit, said real-time clock means, said random access memory storage unit means, said arithmetic and logic unit means, and said digital output means, and
      (vii) means for processing said digital output from said secondary signal processing circuit.

12. A multi-probed metering apparatus as in claim 11 comprising at least a second sonde unit, wherein said second sonde unit comprises:
   (a) a plurality of pick-up means,
   (b) an analog/digital converter means,
   (c) a selector circuit for identifying each of said plurality of second sonde unit pick-up means with which said second sonde unit is associated, said second sonde unit selector circuit interfaces said second sonde unit plurality of pick-up means with said second sonde unit analog/digital converter means, (d) an address selector for identifying said second sonde unit, and (e) primary digital signal processing circuit, said second sonde unit primary digital processing circuit being in bi-directional digital communication with said second sonde unit analog/digital converter means and with said central processing unit secondary digital signal processing circuit, and in uni-directional digital communication with said second sonde unit selector circuit and said second sonde unit address selector.

13. A multi-probed metering apparatus as in claim 12 wherein said second sonde unit further comprises an improved fluid flow-maintaining means integrated into said second sonde unit, said fluid flow-maintaining means comprising:

(a) stirrer control, (b) stirrer driving component, and (c) propeller component fixedly attached to said stirrer driving component, said stirrer control being in uni-directional digital communication with said second sonde unit primary digital signal processing circuit and with said stirrer driving component.

14. A multi-probed metering apparatus as in claim 12 wherein said digital output means is selected from the group consisting of light emitting diode (LED) display, liquid crystal diode (LCD) display, external computer and/or monitoring sources, a digital/analog converter means, and any combination thereof.

15. A multi-probed metering apparatus as in claim 12 wherein said central processing unit random access memory storage unit has the capability of handling between 500 and 5,000,000 bytes of information.

16. A multi-probed metering apparatus as in claim 11 wherein at least one of said plurality of pick-up means comprises:

(a) a monitoring end portion, (b) a signal transmitting end portion, said signal transmitting end portion comprising a means for interconnecting said pick-up means to said sonde unit, and (c) sealing means located between said monitoring end portion and said signal transmitting end portion, said sealing means being dimensioned to prevent the flow of fluid between said pick-up means monitoring end portion and said pick-up means signal transmitting end portion.

17. A multi-probed metering apparatus as in 16 wherein said at least one of said plurality of pick-up means further comprises means for securing said at least one of said plurality of pick-up means to said sonde unit, said securing means being positioned between said pick-up means monitoring end portion and said sealing means.

18. A multi-probed metering apparatus as in claim 11, further comprising a means for calibrating said pick-up means, wherein said calibration means comprises a polyhedrally-shaped calibration cup body having at least two parallel planar surfaces, said calibration cup body defines a plurality of vertically-oriented calibration wells which, while passing through one of said at least two parallel planar surfaces, do not pass through the opposing parallel planar surface, the configuration of the openings in the calibration cup body parallel planar surface through which the calibration wells pass corresponds with the configuration of said plurality of pick-up means in said sonde unit, and said calibration wells being dimensioned such that, when said plurality of pick-up means are introduced therein, the outside wall surfaces of said pick-up means within said calibration wells are spaced apart from said calibration cup body inside wall surfaces defined by said calibration wells.

19. A multi-probed metering apparatus as in claim 18 further comprising a means for measuring the amount of calibration fluid which should be introduced therein.

20. A multi-probed metering apparatus in accordance with claim 18 further comprising a means for preventing cross-contamination of one of said plurality of pick-up means by a calibration solution of another of said plurality of pick-up means.

21. A multi-probed metering apparatus as in claim 18 further comprising a means for fluidly interconnecting a plurality of said calibration wells together.

22. A multi-probed metering apparatus as in claim 18 further defining a well configured and dimensioned to accept a fluid-flow maintaining means integrated into said sonde unit.

23. A sonde comprising a housing, a plurality of discrete sensing electrodes of analog output attached to said housing for sensing a corresponding plurality of parameters to be measured, means for selectably activating each said electrode, said housing comprises:

(a) a built-in, integral stirrer unit, said stirrer unit consisting of:

(i) a liquid agitator portion mounted externally of the housing adjacent the active portions of said electrodes, (ii) an entirely internal agitator drive means, and (iii) an entirely internal agitator drive control means;

(b) a built-in integral microprocessor;

(c) an entirely internal analog-digital converter means for digitizing the analog output generated by said electrodes and passing said digitized output to said microprocessor; and (d) output porting connected to receive said digitized output, said agitator drive control means being electrically controlled by said microprocessor.

24. A sonde as recited in claim 23 wherein one end of each said electrode is mounted in a seat in said housing, said seat and the adjacent said one end of said electrode each being formed with co-operable quick-release coupling means for the ready attachment and release therebetween, and wherein each said electrode having a sealing means for preventing the ingress of liquid to said seat.

25. A sonde as recited in claim 23 wherein said drive means comprises:

(a) a motor having a rotatable magnet with at least one planar surface;

(b) a motor shaft having a longitudinal axis generally perpendicular to said motor magnet at least one planar surface;

(c) a rotary agitator shaft; and (d) a rotatable agitator magnet having at least one planar surface, wherein the longitudinal axis of said agitator shaft is generally perpendicular to said agitator magnet planar surface, and wherein said motor magnet planar surface is in spaced apart alignment with, but magnetically interconnectable to, said agitator magnet planar surface.

26. A sonde as recited in claim 23 further comprising a calibration cup in attachable and detachable configuration with said housing, said cup defining a plurality of calibration wells designed to receive and encompass the lower portion of each said sensing electrode, wherein each said well is provided with fluid identification indicia, and wherein each said well is designed to prevent undesired overflow of liquid from one well into another.

27. A sonde comprising a housing, a plurality of discrete sensing electrodes of analog output attached to said housing for sensing a corresponding plurality of parameters to be measured, and means for selectably activating each said electrode,
   wherein said electrodes have connected thereto an analog/digital converter which is effective to digitize the analog output signal from each electrode,
   wherein said housing comprises a digital signal processor for controlling said means for selectably activating each electrode,
   wherein said housing comprises an output means,
   wherein said digital signal processor is connected for bi-directional digital communication with said analog/digital converter and with said output means,
   wherein said sonde is adapted for bi-directional digital communication through said output means with a discrete apparatus which is effective to process, store and/or display digital data derived from sensing electrodes of at least one other sonde,
   wherein a stirrer is attached to said housing,
   wherein means for rotating said stirrer is located substantially wholly within said housing, and
   wherein said stirrer drive control means is located substantially wholly within said housing and electrically integrated with said digital signal processor.

28. A sonde as recited in to claim 27 wherein said stirrer-rotating means comprises:
   (a) a motor having a rotatable magnet with at least one planar surface;
   (b) a motor shaft having a longitudinal axis generally perpendicular to said motor magnet at least one planar surface;
   (c) a rotary stirrer shaft; and
   (d) a rotatable stirrer magnet having at least one planar surface,
wherein the longitudinal axis of said stirrer shaft is generally perpendicular to said stirrer magnet planar surface, and wherein said motor magnet planar surface is in spaced apart alignment with, but magnetically interconnected to, said stirrer magnet planar surface.

29. A sonde as recited in claim 27 further comprising an address selector which identifies said sonde, said address selector being in uni-directional digital communication with said digital signal processor.

30. A sonde comprising a housing, a plurality of discrete electrodes of analog output attached to said housing for sensing a corresponding plurality of parameters to be measured, and means for selectably activating each said electrode, said housing comprising a calibration cup in attachable and detachable configuration with said housing, wherein said calibration cup defines a plurality of calibration wells designed to receive and encompass the lower portion of said sensing electrode, wherein each said well is provided with liquid identification indicia, and wherein each said well is designed to prevent undesired overflow of liquid from one well into another.

31. A sonde comprising a housing, a plurality of discrete sensing electrodes of analog output attached to said housing for sensing a corresponding plurality of parameters to be measured, and means for selectably activating each said electrode, said housing comprises:
   (a) a built-in, integral stirrer unit, wherein said unit consists of:
      (i) a liquid agitator portion mounted externally of said housing and adjacent the active portions of said electrodes;
      (ii) an entirely internal agitator drive means, and
      (iii) an entirely internal agitator drive control means;
   (b) a built-in, integral microprocessor;
   (c) an entirely internal analog-digital converter means for digitizing the analog output generated by said electrodes and passing said digitized output to said microprocessor; and
   (d) output porting connected to receive said digitized output,
wherein said agitator drive control means is electrically controlled by said microprocessor, wherein one end of each said electrode is mounted in a seat in said housing, said seat and the adjacent said one end of said electrode each being formed with co-operable quick-release coupling means for the ready attachment and release therebetween, and wherein each said electrode having a sealing means for preventing the ingress of liquid into said seat.

* * * * *